United States Patent [19]

Hashim

[11] Patent Number: 4,744,035

[45] Date of Patent: May 10, 1988

[54] INSPECTING TEXTILE PRODUCTS

[75] Inventor: Abdullah Hashim, Leicester, United Kingdom

[73] Assignee: National Research Development Corporation, London, England

[21] Appl. No.: 631,212

[22] Filed: Jul. 16, 1984

[30] Foreign Application Priority Data

Jul. 16, 1983 [GB] United Kingdom ............... 8319281
Oct. 22, 1983 [GB] United Kingdom ............... 8328280

[51] Int. Cl.$^4$ .......................... G06F 15/46; B07C 5/00
[52] U.S. Cl. ...................................... 364/470; 209/576; 209/659; 209/939; 250/563; 356/431; 358/107; 364/507
[58] Field of Search ............... 364/470, 506, 507, 552; 358/106, 107; 356/429–431, 237, 238, 394; 250/559, 562, 563, 571, 572; 209/562–564, 576–579, 585–589, 632, 659, 509, 937, 939; 382/8, 18, 36–38, 51

[56] References Cited

U.S. PATENT DOCUMENTS

| 3,662,341 | 5/1972 | Baumgartner et al. ............ 382/51 |
| 4,071,899 | 1/1978 | Holy ............................... 364/475 X |
| 4,075,604 | 2/1978 | Degasperi ............................ 382/18 |
| 4,110,736 | 8/1978 | Kono ................................... 382/22 |
| 4,132,314 | 1/1979 | von Beckmann et al. .......... 364/526 |
| 4,221,297 | 9/1980 | Lopez et al. .................... 209/939 X |
| 4,351,437 | 9/1982 | Long ............................... 209/939 X |
| 4,365,304 | 12/1982 | Ruhmann et al. ................... 382/51 |
| 4,377,238 | 3/1983 | Wilks et al. ..................... 364/507 X |
| 4,403,294 | 9/1983 | Hamada et al. .................... 364/507 |
| 4,414,566 | 11/1983 | Peyton et al. .................. 209/939 X |
| 4,493,420 | 1/1985 | Dennis ........................... 209/939 X |
| 4,549,205 | 10/1985 | Misaki et al. ................... 209/939 X |

FOREIGN PATENT DOCUMENTS

| 0052813 | 6/1982 | European Pat. Off. . |
| 0058028 | 8/1982 | European Pat. Off. . |
| 1298953 | 12/1972 | United Kingdom . |
| 1392448 | 4/1975 | United Kingdom . |
| 1527600 | 10/1978 | United Kingdom . |
| 2009395 | 6/1979 | United Kingdom . |
| 2020945 | 11/1979 | United Kingdom . |
| 2067326 | 1/1980 | United Kingdom . |
| 2027538 | 2/1980 | United Kingdom . |
| 2031684 | 4/1980 | United Kingdom . |
| 2032618 | 5/1980 | United Kingdom . |
| 2057124 | 3/1981 | United Kingdom . |
| 2087548 | 5/1982 | United Kingdom . |
| 2107858 | 5/1983 | United Kingdom . |

Primary Examiner—Joseph Ruggiero
Attorney, Agent, or Firm—Oblon, Fisher, Spivak, McClelland & Maier

[57] ABSTRACT

Textile articles are inspected for size, defects by forming an image e.g. in a video camera, capturing data representing at least salient features of the image, comparing the data automatically with reference data, and effecting a selection process in accordance with the result of the comparison. Articles e.g. socks, presented as a succession of imperfectly matched items, can be sorted for size e.g. into categories of leg and foot length.

25 Claims, 2 Drawing Sheets

INSPECTING TEXTILE PRODUCTS

BACKGROUND TO THE INVENTION

This invention relates to inspecting textile products such as fabrics of woven, non-woven, knitted or other construction and articles such as garments made therefrom.

Currently, inspection is essentially done by trained hand and eye. Especially in the case of garments, inspection is an intricate and repetitive job, and prone on that account to human error. It is also expensive because of the intensive skilled labour requirement.

"Inspection" can cover a wide range of operations, and a single product can be inspected for a wide variety of faults. Faults for which garments are inspected include dimensional deviations from set standards, non-inclusion or incorrect positioning of trims and components, non-inclusion of stitched seams, incorrect pattern matching, and any of the faults that might be detected in the fabric or fabrics that go to make up the garment which could arise in the manufacture, processing, storage and making up. Fabric itself can be inspected for such things as surface distortions from thin areas resulting from thin yarn, dropped stitches, tuck stitches, broken needles, holes, slub cuts, knot cuts, yarn slubs of unacceptable length, incorrect dimensions, presence of foreign material such as broken needle hooks, colour variation, stains, creases, cracks and barre effects. Inspection for fabric faults should ideally not be left until the garment is inspected, which is wasteful of the labour and additional materials content of the made-up garment.

Techniques exist, of course, for detecting some faults other than by hand and eye. Thin places and holes, for instance, can be detected by sensing photo-optically or otherwise light or other radiation transmitted through a fabric. Broken needle hooks can be detected by passing a fabric over a metal detector. There is currently no general method or universal piece of equipment, however, that can be adapted to detect faults of any description.

But for many inspection processes there is simply no available automatic equipment of any description. One such process is the sizing of garments especially knitted garments such as socks. The sock manufacturing process cannot be controlled so exactly that successive items coming off the same machine are identical in every particular, and this is aggravated where a number of machines produce items to a common nominal size for later pairing, so that two items selected at random from the common delivery of the machine or machines are unlikely to match closely enough to be regarded as a pair.

BRIEF DESCRIPTION OF THE INVENTION

The present invention provides methods and apparatus for inspecting textile products which substantially reduce the skilled labour requirement and which are applicable or adaptable to substantially every inspection and selection process at reasonable capital cost and with considerable improvement in reliability.

The invention comprises a method for inspecting textile products comprising presenting such products to imaging apparatus to form an image thereof, capturing data representing at least salient features of said image, comparing said data automatically with reference data, and effecting a selection process in accordance with the result of such comparison.

Said imaging apparatus may comprise an electronic imaging device such as a television camera or charge coupled device. An image enhancing technique may be used to enhance the quality of the image. For example, improved signal-to-noise ratio may be achieved by combining and averaging information from multiple frames of a video image, especially where the object is static at least for long enough to capture multiple frames. A digitised image may be enhanced by histogram modification techniques, image smoothing may be achieved by filtering out low frequency noise, and the image may be sharpened by known image sharpening algorithms.

Preferably, an image comprising a $512 \times 512$ array of pixels is formed.

The entire image is preferably digitised and stored as digital data in RAM locations of a computer which map on to the image. The data can then be processed in a wide variety of ways by appropriate software and data extracted relative to dimensions and faults by appropriate techniques such as edge finding methods and fault recognition algorithms.

Said reference data may comprise dimensional data, and the method may be used for matching sets of items—such as socks—that are supplied as a collection of imperfectly matched such items, comprising presenting each item in turn to said imaging apparatus to form an image thereof, capturing data representing at least salient dimensional features of said image, and segregating said items into sets of matched items by comparing said captured data with predetermined reference data and effecting a selection process in accordance with the result of such comparison.

Socks will be segregated into pairs, while other items might be segregated into sets of complementary items as, for example, where two different objects are to be used or fitted together and have matching parts.

The items may be directed or gated into different collecting regions. The items may, on the other hand, be tagged with information, such as a matching code derived from said captured data.

For general fault-detection inspection, said reference data may comprise data representative of a fault-free textile product.

Data may be selected from the captured data by a mask function corresponding to a given type of fault and compared with data selected from said reference data by said mask function, said data being selected by scanning said mask function over the captured and reference data.

Said mask function may, at its simplest, define a $2 \times 2$ pixel fault detection module. Three mask functions may define three different sizes of fault detection module—say $2 \times 2$, $4 \times 4$ and $8 \times 8$ pixels—and these functions may be added together heirarchically to produce a variety of fault detection modules corresponding to a wide range of length and width of defects.

A statistic is calculated from each said comparison and tested for its departure from a zero statistic indicative of no difference and hence no fault, a fault being indicated at a certain threshold level of said statistic. Said threshold level may be adjustable whereby to tune the method to an acceptable compromise between missed faults and false alarms.

Said selection process may comprise selecting items which have acceptable fault levels and rejecting others, and may comprise marking faults in the products.

The invention also comprises apparatus for inspecting textile products comprising means presenting such products to imaging apparatus to form an image thereof, data capture means capturing data representing at least salient features of said image, comparison means comparing said captured data automatically with reference data, and selection means effecting a selection process in accordance with the result of such comparison.

When said imaging apparatus comprises a television camera, said data capture means may comprise RAM frame store means storing television frames in digital form.

The apparatus may comprise control means for controlling said camera to image different areas of said products and said control means may be programmable so as automatically to effect a desired sequence of inspection procedures.

The apparatus may comprise means traversing said products past said imaging apparatus.

BRIEF DESCRIPTION OF THE DRAWINGS

Embodiments of methods and apparatus for inspecting textile products according to the invention will now be described with reference to the accompanying drawings, in which.

DETAILED DESCRIPTION OF THE PREFERRED EMBODIMENTS

Figure 1:
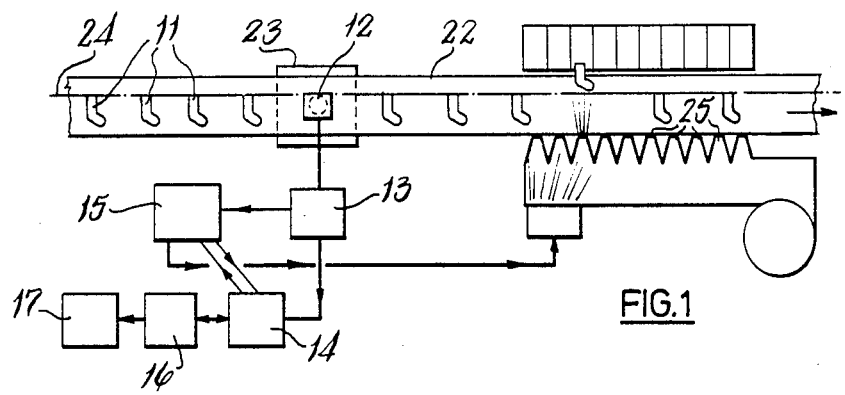
FIG. 1 is a diagrammatic plan view of an inspection station for individual garments with a sorting arrangement.

The drawings illustrate methods for inspecting textile products 11 comprising presenting such products to imaging apparatus 12 in the form of a television camera to form an image thereof.

The video signals from the camera 12 are digitised in an analog-to-digital converter 13 and selected frames captured in a frame store 14 such as a commercially available Gresham Lion 214 supervisor, which can capture, in real time, images from a standard television camera. The frame store 14 is linked to a minicomputer 15 with 64Kbytes of RAM and 2Mbytes of disk storage, and mapping stores 16 and a VDU or TV monitor 17.

Various image enhancing techniques can be used to enhance the quality of the image. Multiple, for example, three frames may be averaged to improve signal-to-noise ratio. The digitised image may be enhanced by histogram modification techniques, smoothed by filtering out low frequency noise and sharpened by known image sharpening algorithms.

With such techniques a 512×512 pixel array image can readily resolve such small fabric faults as dropped stitches, tuck stitches and presence of foreign material such as broken needle hooks. At the same time, larger scale defects such as thin areas, holes, long yarn slubs, incorrect dimensions, colour variation, stains and barre effects can be detected.

Figure 2:
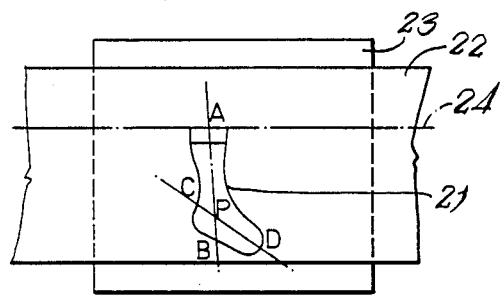
FIG. 2 is a plan view of a sock at an inspection station.

FIGS. 1 and 2 illustrate how dimensional defects can be detected and items sorted according to size. These figures illustrate the method being used for matching socks 21 supplied as a succession of imperfectly matched socks on a translucent conveyor belt 22 which presents each sock 21 in turn to the camera 12 which is located over a back lighting panel 23.

It greatly simplifies the measuring algorithms if the socks 21 can be presented to the camera 12 in substantially constant orientation and position. For this purpose a datum line 24 is drawn on the belt 22. Operatives place the top of the sock on the datum line 24. (The 'top' can be defined either as the upper or lower edge of the welt).

When a sock 21 is in the field of view of the camera 12, which is of course roughly coincident with the panel 23, the imaging, image enhancing and image storing operations are performed. On the stored image, further algorithms are now brought into operation to detect the edges of the sock. An edge detection method for socks has to satisfy the sizing criteria. If the socks are to be classified in 5 mm groups with a precision of ±1 mm on the basis of a full scan size of 500 mm, it is necessary to use a statistical estimate of edge position in the image to better than a single pixel in a 512×512 pixel image. One such estimate is $$\text{Position of edge} = P + (E-B)/(O-B)$$

where
B=light level of background illumination
O=light level of object
E=light level in edge pixel
P=position at beginning of edge pixel.

Figure 3:
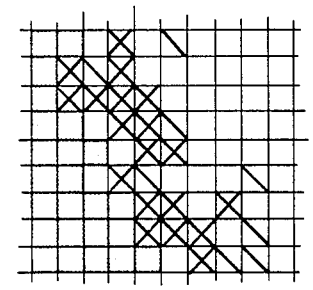
FIG. 3 is a view of a section of video image of an edge.

However, since a sock is not usually a "hard-edged" object, in practice an edge is not seen as a background pixel next to an edge pixel next to an object pixel,—see FIG. 3—and it is necessary to sample a number of pixels extending perpendicularly across the edge in order to compute the centre of change.

Once the edges have been located, the bisectors of the leg (AB) and foot are (CD) computed, and the position P where they intersect—see FIG. 2. The distances AP, PD are useful measures for sock sizing. If three ranges for each of AP and PD are sorted, each, say, of 5 mm spread, nine different categories are required together with a tenth category for socks unacceptably outside one or both permitted variations. FIG. 1 shows a ten gate arrangement with associated blowers 25 under the control of the computer 15.

Figure 4:
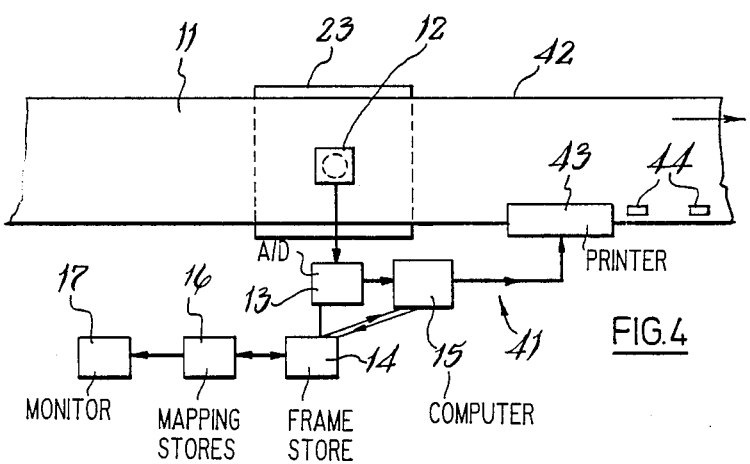
FIG. 4 is a diagrammatic plan view of an inspection station for a travelling web of fabric, with a fault marking arrangement.

FIG. 4 illustrates an inspection station like that illustrated in FIG. 1, but intended for the inspection of a travelling web of fabric and having a fault marking arrangement 41 instead of the sorting arrangement.

The travelling web 42 passes, again, over a back lighting panel and images formed by the camera 12 captured in the frame store 14. As a fault is detected the computer 15 activates a printer 43 to apply a mark 44 to the edge of the web 42 where the fault occurs. The mark 44 can be in the form of an ink-jet printed mark or a self adhesive label and can indicate the nature of the fault, for example, a thin region, incorrect width, slub, dropped stitch, or whatever.

Fabric width is measured exactly as previously described in connection with sock dimensions by locating the fabric edges on the image and computing the distance between them. Fabric faults such as dropped stitches are detected by using a masking technique.

If a 4×2 pixel mask is used, each 4×2 pixel area of the image is examined in turn to detect a departure from the expected image. Such a 4×2 pixel mask is useful for the detection of small defects such as dropped stitches, tuck stitches, presence of foreign matter and so on.

The mask—which is simply a 4×2 pixel representation of what is expected to be seen at any particular location—operates on the representation in the actual (enhanced) image to produce a feature which approaches value zero when there is no defect (i.e. actual is the same as expected) and the value 1 when the mask is coincident with a defect.

Figure 5:
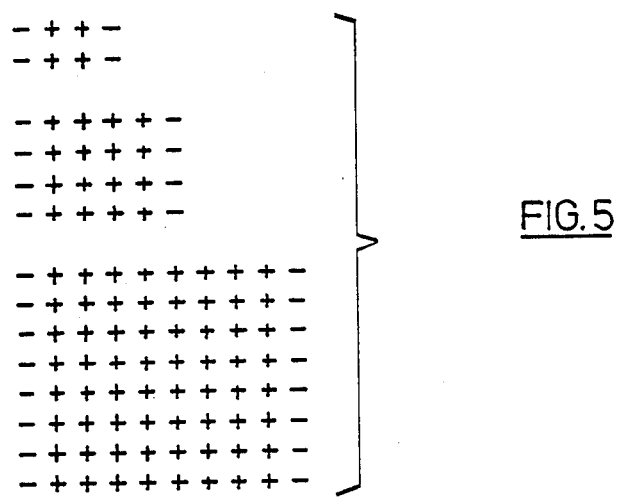
FIG. 5 is a representation of three masks for use in defect detection.

As shown in FIG. 5, three different masks of different sizes are shown which are useful in the detection of small width, medium width and wide defects.

Figure 6:
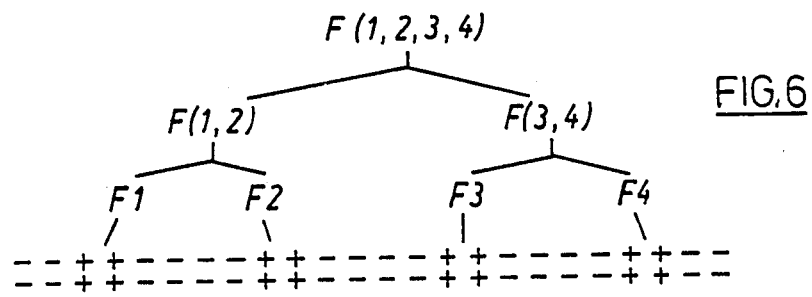
FIG. 6 is a representation of how one of the masks shown in FIG. 4 can be used in a system for detecting different kinds of faults.

As further seen in FIG. 6, masks can be arranged in a heirarchical tree structure in order to detect larger defects. Thus instead of first searching the image for 2×2 pixel sized defects, then for 4×2 defects, then for 8×2, 16×2, 32×2 defects and so on, the image can be examined once for 2×2 pixel defects, then the resulting features combined at different levels in the tree structure.

At any node (F1, F2, F3, F(1,2), F(1,2,3,4) etc.) the expected value of the feature is zero for no defect. A null hypothesis of no defect is tested by the deviation of the feature from zero. Thus for a point defect such as a dropped stitch, node F1 might have a feature value approaching 1, while F2, F3, F4 etc. are zero. If, however, F1, F2, F3 the value 1, the feature at node F(1,2,3,4) would approach 1 and this would indicate a line feature—such as a crease—rather than a succession of dropped or tuck stitches.

The provision of different mask sizes maximises sensitivity to features of different width. Thus, while the low width mask might tend to identify a number of adjacent line features as such, this interpretation would be overridden by the wide mask that might show these features up as a thin area or a hole or a stain depending upon the light level.

The deviation of the feature value from zero is tested by a suitable statistical test such as the t-test for significance. The significance level can be pre-selected to give, in particular circumstances, an acceptable compromise between missed faults and false alarms.

The expected value in a mask is input from a sample of fault free fabric or a fault free article used as a standard. Obviously faults are easier to detect in a plain fabric than in a patterned fabric, for which the software would be required first to "align" the actual and standard sample images.

So far, what have been described are techniques where measurement and fault identification have been effected entirely by algorithmic processes on a captured image. It is possible, however, also to use camera-pointing techniques for measurement, say, in which a servo-controlled scanning camera locates a salient feature—a toe, for example, of a sock—and records its coordinates, then locates another such salient feature and records its coordinates, the dimensions of the item being computed from the coordinates.

Figure 7:
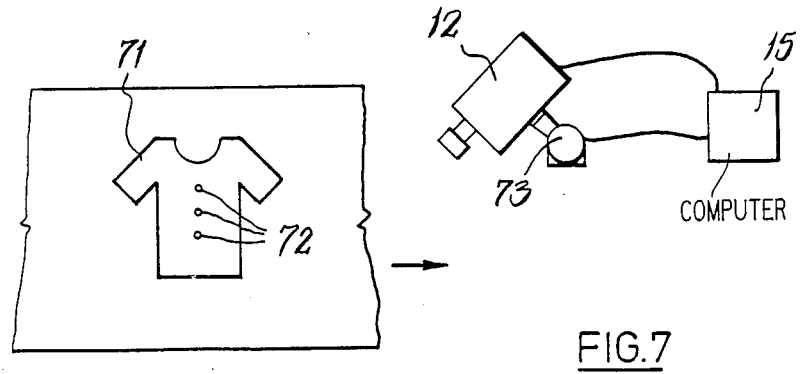
FIG. 7 is a diagrammatic view of another arrangement at an inspection station.

FIG. 7 shows such a system in which made-up garments 71 are passed on a belt beneath a scanning camera 11 having a zoom lens. Each garment 71 is arrested beneath the camera 11 to capture its image. The computer 15 checks that salient features such as buttons 72 are present and correctly positioned by comparison with a standard reference image. Having located the buttons, the computer then actuates the servo-motor 73 to point the camera at each button in turn, zooming-in to obtain a high resolution image of the button which is checked against another standard reference image to ensure that the button is properly sewn by ensuring that the thread holes are filled.

What I claim is:

1. A method for processing textile items having elongate portions defining intersecting bisectors, said items being supplied as a collection of imperfectly matched such items, comprising the steps of
   (a) consistently orienting said items,
   (b) optically capturing data representing at least salient dimensional features of said consistently oriented items as a function of at least the lengths of said bisectors,
   (c) comparing said data automatically with reference data, said reference data including lengths of said bisectors for sets of said items,
   (d) effecting a selection process in accordance with the result of such comparison, and
   (e) segregating said selected items into sets of matched items by said comparison and selection processes.

2. A method according to claim 1, in which said optically captured data is captured by means of a television camera.

3. A method according to claim 2, wherein the quality of the optically captured data is enhanced with an image enhancing technique.

4. A method according to claim 1, wherein said optically captured data is formed into an image comprising a 512×512 array of pixels.

5. A method according to claim 1, wherein said optically captured data is digitized and stored as digital data in RAM locations of a computer which map onto the image.

6. A method according to claim 1, in which said items are segregated into pairs of substantially identical items.

7. A method according to claim 1, in which said items are segregated into sets of complementary items.

8. A method according to claim 1, in which the items are directed into collecting regions according to size.

9. A method according to claim 1, in which the items are tagged with information derived from said captured data.

10. A method according to claim 1, used for sizing socks, said dimensional data comprising the distances from the intersection of the bisectors of the foot and leg to the toe and to the top of the sock.

11. A method according to claim 1, in which said reference data comprise data representative of a fault-free textile product, and the method is used to detect faults in similar products.

12. A method according to claim 11, in which data is selected from the captured data by a mask function corresponding to a given type of fault and compared with data selected from said reference data by said mask function, said data being selected by scanning said mask function over the captured and reference data.

13. A method according to claim 12, in which said mask function defines a 2×2 pixel fault detection module.

14. A method according to claim 12, in which three mask functions define three different sizes of fault detection module and mask functions are added to produce larger and differently shaped fault detection modules.

15. A method according to claim 12, in which a statistic is calculated from the said comparison and tested for its departure from a zero statistic indicative of no difference and hence no fault, a fault being indicated at a certain threshold level of said statistic.

16. A method according to claim 15, said threshold level being adjustable whereby to tune the method to an acceptable compromise between missed faults and false alarms.

17. A method according to claim 11, in which said selection process comprises selecting items which have acceptable fault levels and rejecting others.

18. A method of claim 11, in which said selection process comprises marking faults on the products.

19. A method according to claim 1 wherein said items are socks.

20. Apparatus for processing textile items having elongate portions defining intersecting bisectors, said items being supplied as a collection of imperfectly matched such items, comprising in combination:
(a) means for consistently orienting said items,
(b) optical data capture means for capturing data representing at least salient dimensional features of said consistently oriented items as a function of at least the lengths of said bisectors,
(c) comparison means for comparing said captured data automatically with reference data, including lengths of said bisectors for sets of said items,
(d) selection means adapted to select items from said collection in accordance with the result of said comparison and segregate said selected items into sets of matched items.

21. Apparatus according to claim 20, wherein said optical data capture means comprises a television camera.

22. Apparatus according to claim 20, said data capture means comprising RAM frame store means storing television frames in digital form.

23. Apparatus according to claim 20, comprising control means for controlling said optical data capture means to image different areas of said products.

24. Apparatus according to claim 23, said control means being programmable so as automatically to effect a desired sequence of inspection procedures.

25. Apparatus according to claim 20, comprising means traversing said products past said optical data capture means.

* * * * *